(12) United States Patent
Sun

(10) Patent No.: US 11,357,389 B1
(45) Date of Patent: Jun. 14, 2022

(54) SUB-MILLIMETER TUNING FOCUS APPARATUS FOR A MEDICAL DEVICE

(71) Applicant: Yingjie Sun, Irvine, CA (US)

(72) Inventor: Yingjie Sun, Irvine, CA (US)

(*) Notice: Subject to any disclaimer, the term of this patent is extended or adjusted under 35 U.S.C. 154(b) by 224 days.

(21) Appl. No.: 16/689,634

(22) Filed: Nov. 20, 2019

Related U.S. Application Data

(60) Provisional application No. 62/770,094, filed on Nov. 20, 2018.

(51) Int. Cl.
*A61B 1/00* (2006.01)
*A61B 1/05* (2006.01)
*G02B 23/24* (2006.01)

(52) U.S. Cl.
CPC ........ *A61B 1/00188* (2013.01); *A61B 1/0014* (2013.01); *A61B 1/00096* (2013.01); *A61B 1/00133* (2013.01); *A61B 1/05* (2013.01); *G02B 23/2438* (2013.01)

(58) Field of Classification Search
CPC .............. A61B 1/00188; A61B 1/0019; A61B 1/00163; A61B 1/00096; A61B 1/00066; A61B 1/00133; A61B 1/0014; A61B 1/05; A61B 1/051; A61B 1/055; A61B 1/04; A61B 1/042; A61B 1/045; A61B 1/0052; A61B 1/0057; G02B 23/24; G02B 23/2407; G02B 23/243; G02B 23/2438; G02B 23/2446; G02B 23/2453; G02B 23/2476; G02B 23/2484; G02B 23/2492

USPC ................. 600/160, 163, 174, 109, 112, 167
See application file for complete search history.

(56) References Cited

U.S. PATENT DOCUMENTS

| 5,575,754 | A | * | 11/1996 | Konomura | ............. | G01B 11/02 356/241.6 |
|---|---|---|---|---|---|---|
| 5,662,584 | A | * | 9/1997 | Hori | .................... | A61B 1/00096 348/65 |
| 2010/0245549 | A1 | * | 9/2010 | Allen | ................. | A61B 1/00193 348/65 |
| 2014/0146142 | A1 | * | 5/2014 | Duret | ................. | A61B 1/00158 348/47 |
| 2014/0187863 | A1 | * | 7/2014 | Lin | ........................ | A61B 1/042 600/131 |
| 2020/0315444 | A1 | * | 10/2020 | Ramanujam | ....... | A61B 1/00016 |

* cited by examiner

*Primary Examiner* — Ryan N Henderson
*Assistant Examiner* — Pamela F Wu
(74) *Attorney, Agent, or Firm* — Plager Schack LLP; Mark H. Plager; Naomi Mann

(57) ABSTRACT

A tuning focus apparatus designed for use with a camera coupled to a medical device is provided. The camera includes a base housing for storing an image sensor and an optical lens. The tuning focus apparatus includes a gear housing coupled to the base housing, a drive gear rotatably mounted to the gear housing, a driven gear rotatably mounted to the gear housing and connected to the drive gear, a gear rack disposed in the base housing and engaged with the driven gear, and a board coupled to the gear rack and designed to secure the image sensor thereon. Rotational movement of the drive gear drives the driven gear to slidably adjust the gear rack, thereby adjusting a separation distance between the image sensor and optical lens.

10 Claims, 4 Drawing Sheets

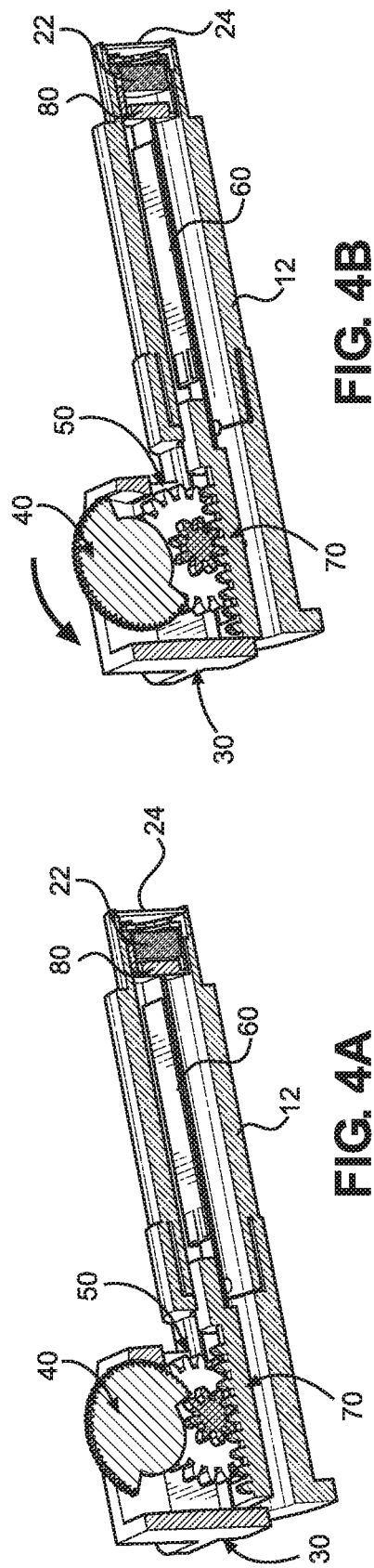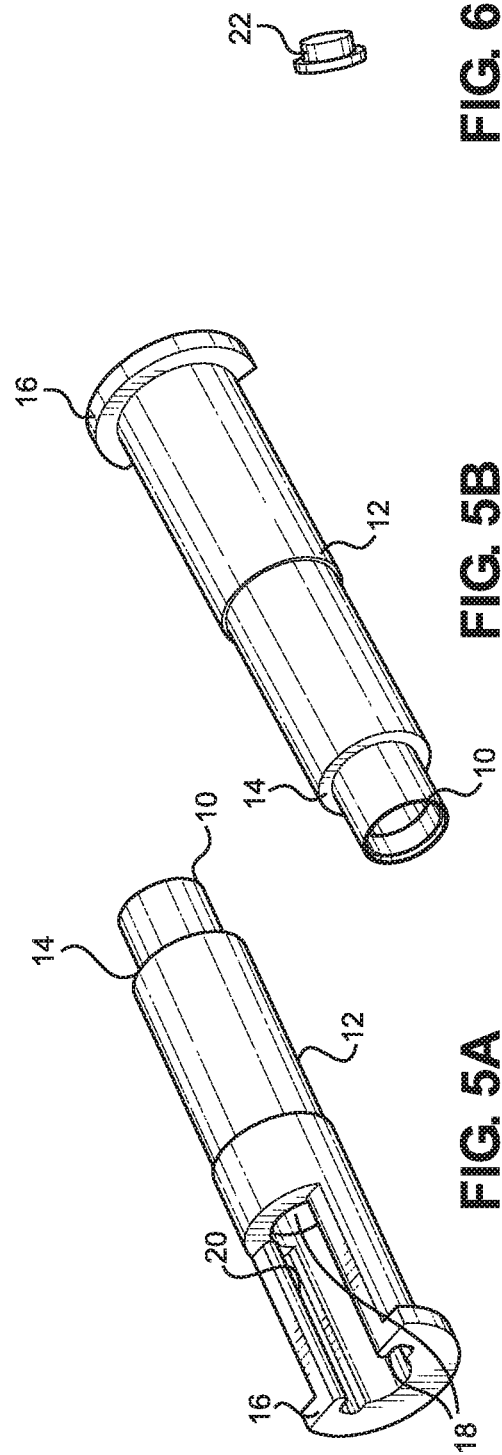

SUB-MILLIMETER TUNING FOCUS APPARATUS FOR A MEDICAL DEVICE

RELATED APPLICATION

The application claims priority to provisional patent application U.S. Ser. No. 62/770,094 filed on Nov. 20, 2018, the entire contents of which is herein incorporated by reference.

BACKGROUND

The embodiments herein relate generally to cameras for medical devices. More specifically, embodiments of the invention are directed to a sub-millimeter tuning focus apparatus for cameras used in medical devices such as endoscopes and otoscopes.

Small diameter cameras used in medical devices such as endoscopes and otoscopes have limited space to house components including the optical lens and image sensor. As such, the focal distance in these cameras is limited due to the cramped space within the camera housing. Current cameras for these medical devices comprise a focus adjusting system that changes the position of the optical lens relative to the image sensor to adjust the distance between the lens and image sensor. In many instances, these systems comprise auto-focusing lens. These systems are complex and expensive.

As such, there is a need in the industry for a tuning focus apparatus for a medical device such as an endoscope and otoscope that addresses the limitations of the prior art, which provides a simple, low-cost and easy to operate manual solution that adjusts the separation distance between the camera's optical lens and image sensor. There is a further need for the tuning focus apparatus to adjust the position of the image sensor relative to the optical lens of the camera.

SUMMARY

In certain embodiments, a tuning focus apparatus configured for use with a camera coupled to a medical device is provided. The camera comprises a base housing for storing an image sensor and an optical lens. The tuning focus apparatus is configured to slidably adjust the image sensor relative to the optical lens to perform a focus procedure. The tuning focus apparatus comprises a gear housing coupled to the base housing, a drive gear rotatably mounted to the gear housing, a driven gear rotatably mounted to the gear housing and operably connected to the drive gear, a gear rack disposed in the base housing and comprising a plurality of teeth engaged with the driven gear, and a board disposed in the base housing and coupled to the gear rack, the board configured to secure the image sensor thereon, wherein rotational movement of the drive gear in a first direction drives the driven gear to slidably adjust the gear rack in a first direction, thereby increasing a separation distance between the image sensor and optical lens, wherein rotational movement of the drive gear in a second direction drives the driven gear to slidably adjust the gear rack in a second direction, thereby decreasing the separation distance between the image sensor and optical lens.

BRIEF DESCRIPTION OF THE FIGURES

The detailed description of some embodiments of the invention will be made below with reference to the accompanying figures, wherein the figures disclose one or more embodiments of the present invention.

FIG. 4A depicts a perspective cross-sectional view of certain embodiments of the tuning focus apparatus;

FIG. 4B depicts a perspective cross-sectional view of certain embodiments of the tuning focus apparatus illustrating the rotation of drive gear assembly 40;

FIG. 5A depicts a top perspective view of certain embodiments of the tuning focus apparatus illustrating camera base housing 12;

FIG. 5B depicts a bottom perspective view of certain embodiments of the tuning focus apparatus illustrating camera base housing 12;

FIG. 6 depicts a perspective view of certain embodiments of the tuning focus apparatus;

DETAILED DESCRIPTION OF CERTAIN EMBODIMENTS

Figure 1A:
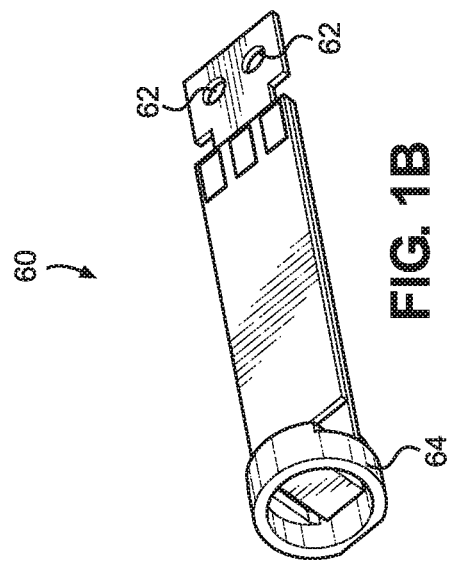
FIG. 1A depicts a top perspective view of certain embodiments of the tuning focus apparatus.
Figure 1B:
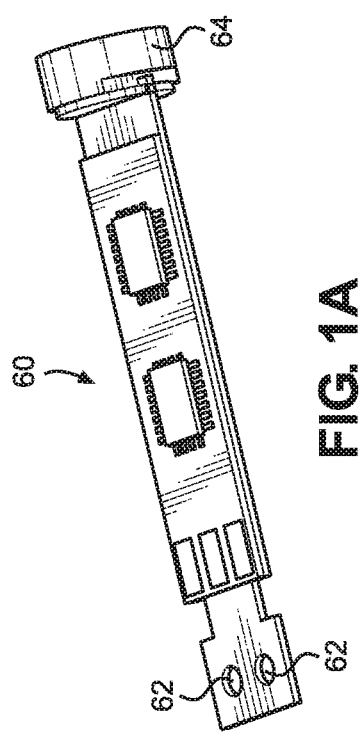
FIG. 1B depicts a bottom perspective view of certain embodiments of the tuning focus apparatus.
Figure 2:
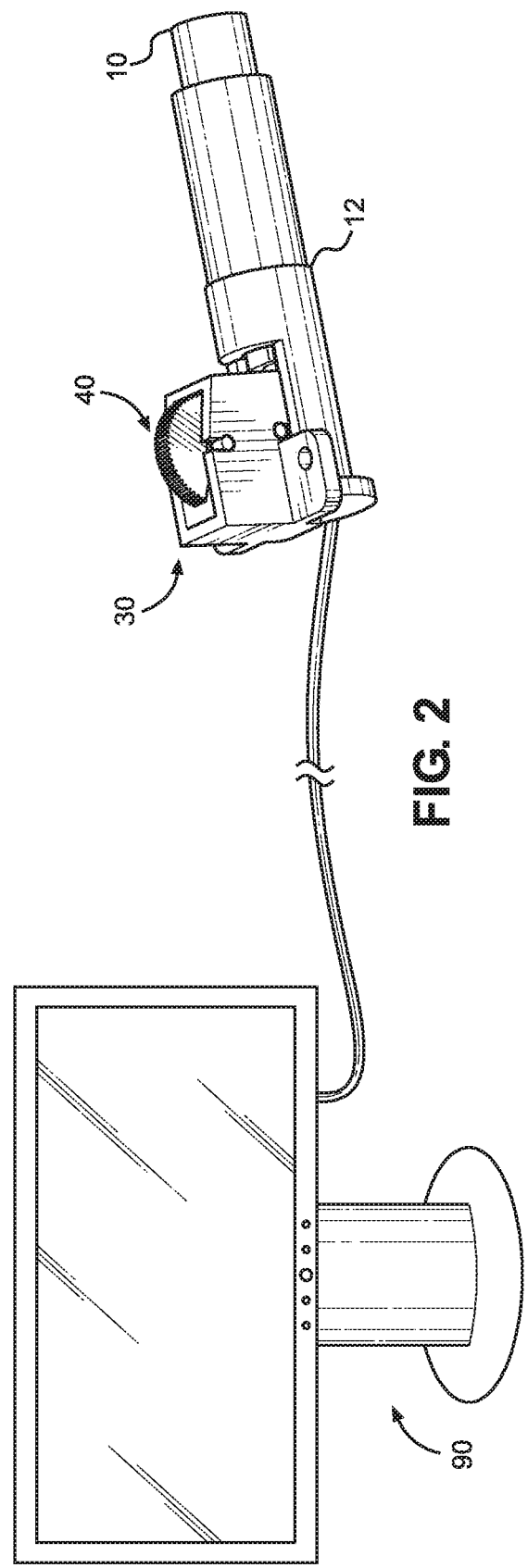
FIG. 2 depicts a perspective view of certain embodiments of the tuning focus apparatus shown in use.
Figure 3:
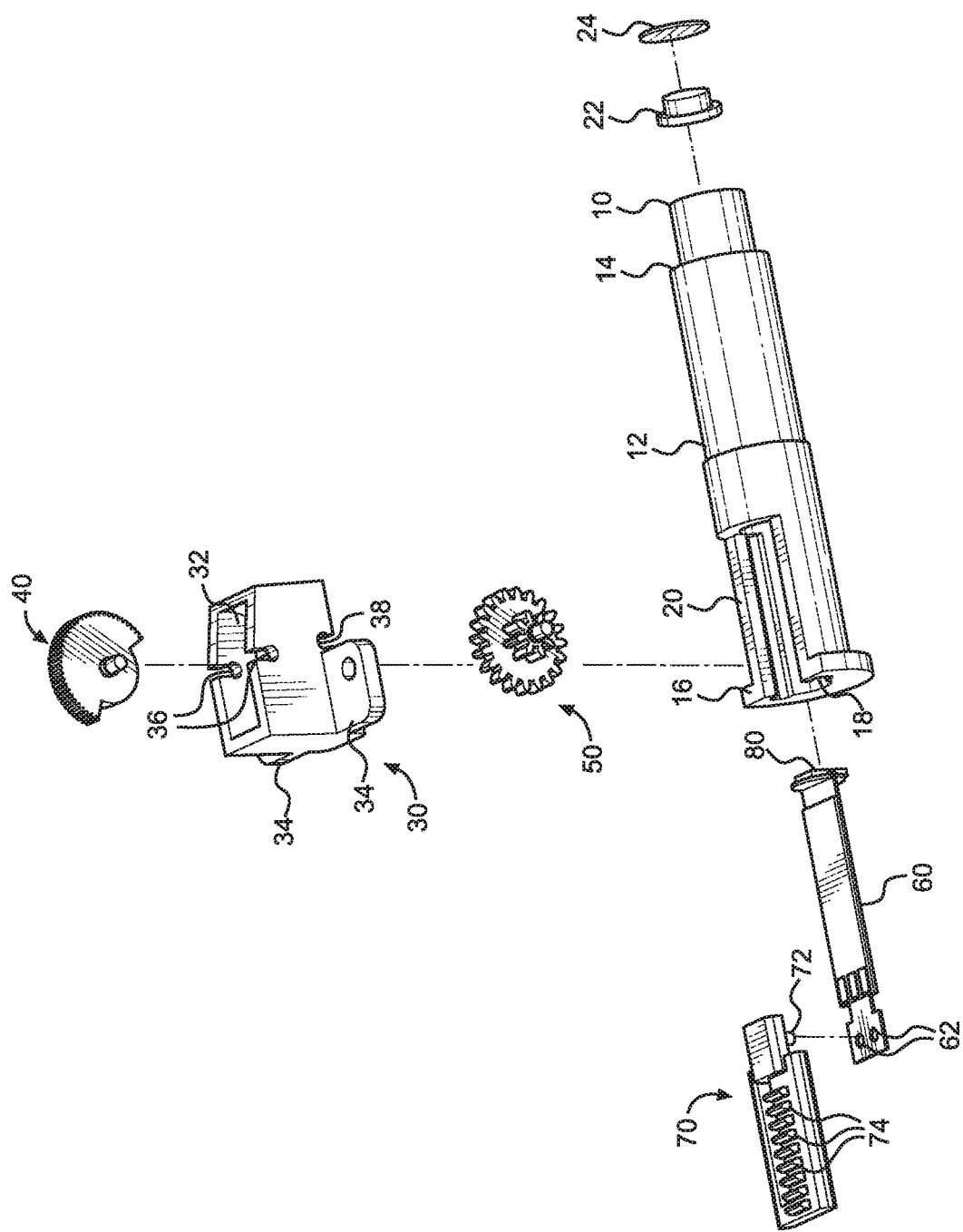
FIG. 3 depicts an exploded view of certain embodiments of the tuning focus apparatus.

In certain embodiments of the invention as depicted in FIGS. 1-4, the tuning focus apparatus is configured for use with a camera of an otoscope, endoscope or other medical device. In one embodiment, the tuning focus apparatus is used with a medical device such as otoscope 10 and a camera comprising camera base housing 12, optical lens 22 and image sensor 80. Otoscope 10 is coupled to camera base housing 12 as depicted in FIGS. 2-3.

In certain embodiments as depicted in FIGS. 2-5, camera base housing 12 comprises a tubular member with first end 14, second end 16 and internal cavity 18. Upper cutout 20 partially extends from second end 16 to an intermediate portion of camera base housing 12, and is continuously connected to internal cavity 18 of camera base housing 12. In one embodiment as depicted in FIG. 4, optical lens 22 of the camera is disposed within otoscope 10 and/or camera base housing 12. Optical lens 22 can be any type of lens known in the field. In one embodiment, lens protector 24 is coupled to otoscope 10 and/or camera base housing 12. Lens protector 24 is made from any transparent material such as glass or other materials.

In a preferred embodiment, camera base housing 12 is made from aluminum. However, camera base housing 12 can be made from other materials or combination of materials including, but not limited to, plastic, other metals, wood and the like. In one embodiment, camera base housing 12 is coupled to and integrated with otoscope 10. In an alternative embodiment, camera base housing 12 is a separate component that can be attached to or detached from otoscope 10. It shall be appreciated that otoscope 10 can be any type known in the field.

Figure 7B:
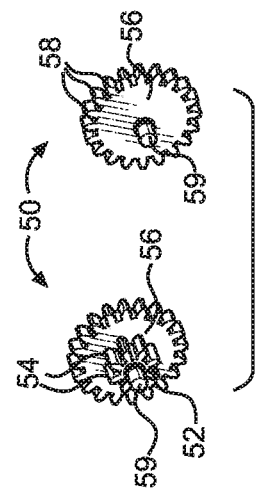
FIG. 7B depicts front and rear perspective views of certain embodiments of the tuning focus apparatus illustrating driven gear assembly 50.
Figure 7D:
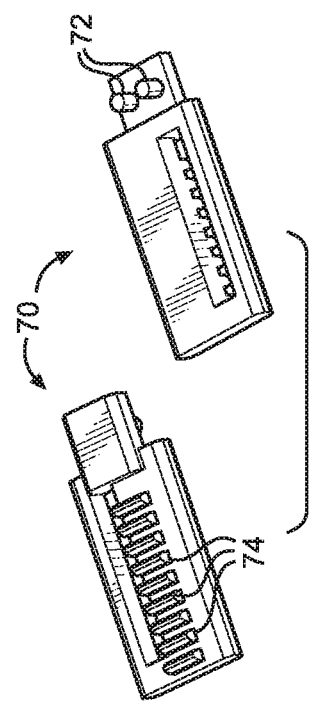
FIG. 7D depicts front and rear perspective views of certain embodiments of the tuning focus apparatus illustrating gear rack 70.
Figure 7E:
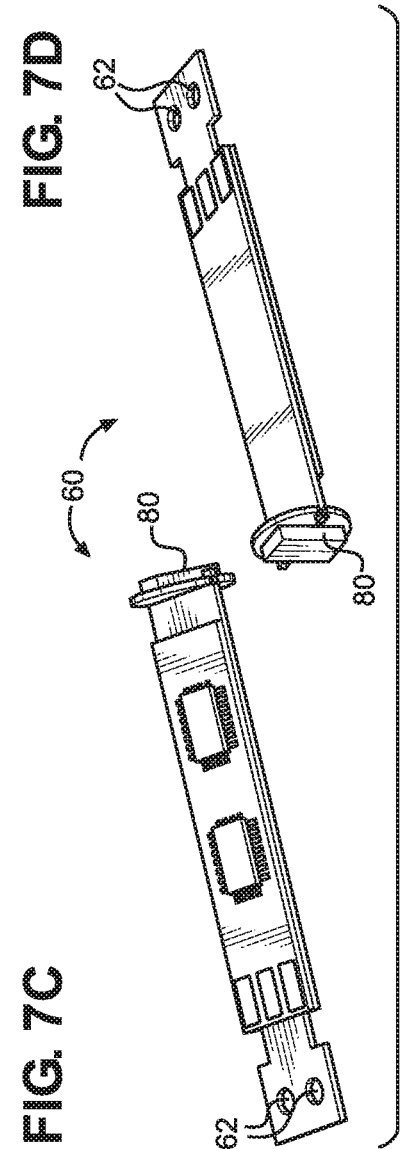
FIG. 7E depicts front and rear perspective views of certain embodiments of the tuning focus apparatus illustrating sensor board 60.

In certain embodiments as depicted in FIGS. 2-3, the tuning focus apparatus generally comprises gear housing 30, drive gear assembly 40, driven gear assembly 50, sensor board 60 and gear rack 70. In one embodiment as depicted in FIGS. 2-3 and 7C, gear housing 30 comprises a body member having opening 32, a pair of lower tabs 34, a pair of upper post openings 36 and a pair of lower post openings 38. Opening 32 extends from the top to the bottom of gear housing 30. In a preferred embodiment, gear housing 30 is preferably made from plastic. However, gear housing 30 can be made from alternative materials such as metal, wood or other materials.

As depicted in FIGS. 2-3, gear housing 30 is coupled to upper cutout 20 of camera base housing 12 by mechanical fasteners, an adhesive and/or other alternative fastening components. Gear housing 30 is configured to house drive gear assembly 40 and driven gear assembly 50.

Figure 7A:
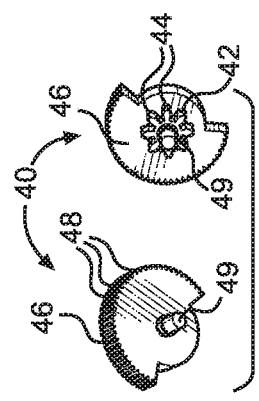
FIG. 7A depicts front and rear perspective views of certain embodiments of the tuning focus apparatus illustrating drive gear assembly 40.
Figure 7C:
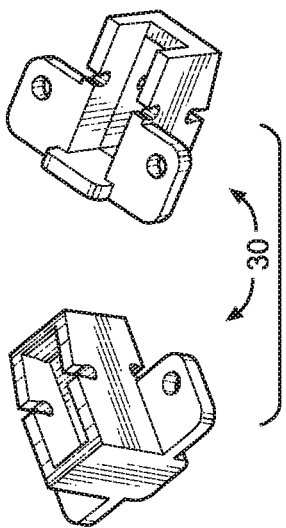
FIG. 7C depicts front and rear perspective views of certain embodiments of the tuning focus apparatus illustrating gear housing 30.

In certain embodiments as depicted in FIGS. 2-3 and 7A, drive gear assembly 40 is rotatably mounted to gear housing 30 and comprises upper small drive gear 42 coupled to upper large drive gear 46 by drive gear post 49. Upper small drive gear 42 comprises upper small gear teeth 44 and upper large drive gear 46 comprises upper large drive gear teeth 48. Upper large drive gear 46 comprises a first radius that is larger than a second radius of upper small drive gear 42. Drive gear post 49 extends through the pair of upper post openings 36 in gear housing 30 to rotatably mount drive gear assembly 40 to gear housing 30.

In certain embodiments as depicted in FIGS. 3-4A and 7B, driven gear assembly 50 is rotatably mounted to gear housing 30 and comprises lower small driven gear 52 coupled to lower large driven gear 56 by driven gear post 59. Lower small driven gear 52 comprises lower small gear teeth 54 and lower large driven gear 56 comprises lower large driven gear teeth 58. Lower large driven gear 56 comprises a third radius that is larger than a fourth radius of lower small driven gear 52.

Driven gear post 59 extends through the pair of lower post openings 38 in gear housing 30 to rotatably mount driven gear assembly 50 to gear housing 30. In this embodiment as depicted in FIG. 4A, upper small gear teeth 44 of upper small drive gear 42 engages with lower large driven gear teeth 58 of lower large driven gear 56.

It shall be appreciated that the components of drive gear assembly 40 and driven gear assembly 50 can be made from various materials known in the field including, but not limited to, metal, plastic, wood or other materials. The shape and dimensions of drive gear assembly 40 and driven gear assembly 50 can vary in different embodiments of the invention.

In certain embodiments as depicted in FIGS. 4 and 7D, gear rack 70 is disposed in internal cavity 18 of camera base housing 12 and comprises a plurality of teeth 74 that engages with lower small gear teeth 54 of lower small driven gear 52. In one embodiment, gear rack 70 comprises a pair of protrusions 72. Gear rack 70 can be made from various materials known in the field including, but not limited to, metal, plastic, wood or other materials.

In certain embodiments as depicted in FIGS. 1, 3-4 and 7E, sensor board 60 is disposed in internal cavity 18 of camera base housing 12 and comprises a second end having a pair of openings 62 and a first end configured to permit the attachment of image sensor 80 thereto. The pair of protrusions 72 of gear rack 70 engages with the pair of openings 62 of sensor board 60 to couple the components together. In this configuration, sensor board 60 maintains image sensor 80 in proximity to optical lens 22 of the camera.

It shall be appreciated that image sensor 80 may be any type of sensor commonly used in the camera industry. In certain embodiments, sensor board 60 may comprise any number of circuits, electrical components and the like, to implement the functionality of image sensor 80 and the camera. In one embodiment as depicted in FIG. 7E, image sensor 80 is exposed on the first end of sensor board 60. In an alternative embodiment as depicted in FIGS. 1A-1B, the first end of sensor board 60 comprises covering 64, which extends around image sensor 80.

In operation, the camera of otoscope 10 or alternative medical device is operated in a conventional manner as is known in the field. In one embodiment, the camera of otoscope 10 or alternative medical device may be connected to computing device 90 as depicted in FIG. 2. Computing device 90 is used to view, analyze and/or perform other functions with regards to data generated by the camera and/or otoscope 10.

A user manually rotates drive gear assembly 40 as needed to slidably adjust image sensor 80 relative to optical lens 22. This adjusts the separation distance between image sensor 80 and optical lens 22 to perform a focus procedure of the camera.

In one embodiment as depicted in FIG. 4B, rotational movement of upper large drive gear 46 of drive gear assembly 40 in a first direction as depicted by the arrow transfers through upper small drive gear 42 to drive lower large driven gear 56 of driven gear assembly 50. This allows lower small driven gear 52 to engage teeth 74 of gear rack 70, which slidably adjusts sensor board 60 to increase the separation distance between image sensor 80 and optical lens 22. Rotational movement of upper large drive gear 46 of drive gear assembly 40 in an opposite second direction reverses the movement of the gears in drive and driven gear assemblies 40, 50, which slidably adjusts sensor board 60 to decrease the separation distance between image sensor 80 and optical lens 22. This is illustrated in FIG. 4A.

In one embodiment, upper large drive gear 46 of drive gear assembly 40 rotates within the approximate range of 0-80 degrees. This range of motion allows drive and driven gear assemblies 40, 50 to adjust the separation distance between image sensor 80 and optical lens 22 within the approximate range of 0 millimeters-1 millimeters.

In an alternative embodiment, the gear ratios between drive and driven gear assemblies 40, 50 and gear rack 70 can be adjusted to alter the moving range of image sensor 80 to accommodate different camera lenses and user requirements. In one embodiment, rotational movement of drive and driven gear assemblies 40, 50 adjusts the separation distance between image sensor 80 and optical lens 22 within the approximate range of 0 millimeters-5 millimeters. In an alternative embodiment, each gear assembly in drive and driven gear assemblies 40, 50 can have any alternative number of gears.

It shall be appreciated that the components of the tuning focus apparatus described in several embodiments herein may comprise any alternative known materials in the field and be of any color, size and/or dimensions. It shall be appreciated that the components of the tuning focus apparatus described herein may be manufactured and assembled using any known techniques in the field.

Persons of ordinary skill in the art may appreciate that numerous design configurations may be possible to enjoy the functional benefits of the inventive systems. Thus, given the wide variety of configurations and arrangements of embodiments of the present invention, the scope of the invention is reflected by the breadth of the claims below rather than narrowed by the embodiments described above.

What is claimed is:

1. A medical device comprising:
   a camera including a base housing, the base housing comprising a first end, a second end, an internal cavity, and an upper cutout partially extending from the second end to an intermediate portion of base housing, said upper cutout further being continuously connected to the internal cavity of the base housing;
   a gear housing coupled to the base housing;
   a drive gear rotatably mounted to the gear housing;
   a driven gear rotatably mounted to the gear housing and operably connected to the drive gear;
   a gear rack disposed in the base housing and comprising a plurality of teeth engaged with the driven gear; and
   a sensor board disposed in the base housing and coupled to the gear rack, the sensor board including an image sensor secured thereon;
   wherein rotational movement of the drive gear in a first direction drives the driven gear to slidably adjust the gear rack in a first direction, thereby increasing a separation distance between the image sensor and an optical lens coupled to the camera proximate said first end of the base housing, wherein rotational movement of the drive gear in a second direction drives the driven gear to slidably adjust the gear rack in a second direction, thereby decreasing the separation distance between the image sensor and optical lens,
   wherein the gear housing comprises a body member having an opening which extends from a top end to a bottom end of the gear housing, and is coupled to the upper cutout of the base housing at the bottom end of the gear housing above the gear rack,
   wherein the plurality of teeth of the gear rack are disposed on a top side of the gear rack, the plurality of teeth being exposed through said upper cutout of the base housing of the camera,
   and wherein the driven gear extends downwards from the bottom end of the gear housing to engage said plurality of teeth of the gear rack.

2. The medical device of claim 1, wherein the drive gear comprises a first upper gear coupled to a second upper gear by a first post and the driven gear comprises a first lower gear coupled to a second lower gear by a second post, the first upper gear comprising a first set of teeth, the second upper gear comprising a second set of teeth, the first lower gear comprising a third set of teeth and the second lower gear comprising a fourth set of teeth.

3. The medical device of claim 2, wherein the second set of teeth of the second upper gear engages with the third set of teeth of the first lower gear, and the fourth set of teeth of the second lower gear engages with the plurality of teeth of the gear rack.

4. The medical device of claim 3, wherein the first upper gear comprises a first radius that is greater than a second radius of the second upper gear, wherein the first lower gear comprises a third radius that is greater than a fourth radius of the second lower gear.

5. The medical device of claim 3, wherein the gear housing comprises a pair of upper openings configured to receive the first post of the drive gear therein and a pair of lower openings configured to receive the second post of the driven gear therein.

6. The medical device of claim 5, wherein the rotational movement of the drive gear adjusts the separation distance between the image sensor and optical lens within the approximate range of 0 millimeters-5 millimeters.

7. The medical device of claim 5, wherein the rotational movement of the drive gear adjusts the separation distance between the image sensor and optical lens within the approximate range of 0 millimeters-1 millimeters.

8. The medical device of claim 7, wherein the gear rack comprises a protrusion that engages with a corresponding opening located on a second end of the board.

9. The medical device of claim 8, wherein the image sensor is secured to the sensor board at a first end of the sensor board.

10. The medical device of claim 9, wherein the gear housing is directly coupled to the base housing of the camera by a mechanical fastener.

* * * * *